US00PP14712P2

(12) United States Plant Patent
Vlielander

(10) Patent No.: US PP14,712 P2
(45) Date of Patent: Apr. 20, 2004

(54) KALANCHOE PLANT NAMED 'LA DOUCE'

(50) Latin Name: *Kalanchoe blossfeldiana*
Varietal Denomination: La Douce

(75) Inventor: Ike Vlielander, Maasland (NL)

(73) Assignee: Fides Goldstock Breeding B.V., Maasland (NL)

( * ) Notice: Subject to any disclaimer, the term of this patent is extended or adjusted under 35 U.S.C. 154(b) by 0 days.

(21) Appl. No.: 10/421,331

(22) Filed: Apr. 23, 2003

(51) Int. Cl.[7] ..... A01H 5/00
(52) U.S. Cl. ..... Plt./339
(58) Field of Search ..... Plt./339

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Kalanchoe plant named 'La Douce', characterized by its numerous multi-petalled pink-colored flowers; upright, uniform and compact plant habit; freely branching growth habit; dark green glossy leaves; and excellent postproduction longevity.

1 Drawing Sheet

Botanical classification/cultivar designation: *Kalanchoe blossfeldiana* cultivar La Douce.

BACKGROUND OF THE INVENTION

The present invention relates to a new and distinct cultivar of Kalanchoe plant, botanically known as *Kalanchoe blossfeldiana,* and hereinafter referred to by the name 'La Douce'.

The new Kalanchoe is a product of a planned breeding program conducted by the Inventor in De Lier, The Netherlands. The objective of the breeding program is to create new Kalanchoes with multi-petalled flowers.

The new Kalanchoe originated from a cross-pollination made by the Inventor in September, 1999, of the Kalanchoe cultivar Leonardo, disclosed in U.S. Plant Pat. No. 13,365, as the female, or seed, parent with the Kalanchoe cultivar Alexandra, disclosed in U.S. Plant Pat. No. 10,262, as the male, or pollen, parent. The new Kalanchoe was selected by the Inventor in a controlled environment from the resultant progeny of the cross-pollination on the basis of its multi-petalled flowers.

Asexual reproduction of the new Kalanchoe by terminal vegetative cuttings taken at De Lier, The Netherlands, since 2000 has shown that the unique features of this new Kalanchoe are stable and reproduced true to type in successive generations.

BRIEF SUMMARY OF THE INVENTION

The cultivar La Douce has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'La Douce'. These characteristics in combination distinguish 'La Douce' as a new and distinct cultivar:

1. Numerous multi-petalled pink-colored flowers.
2. Upright, uniform and compact plant habit.
3. Freely branching growth habit.
4. Dark green glossy leaves.
5. Excellent postproduction longevity.

Plants of the new Kalanchoe are most similar to plants of the female parent, the cultivar Leonardo. However, plants of the new Kalanchoe differ from plants of the cultivar Leonardo primarily in flower color as plants of the new Kalanchoe have pink-colored flowers whereas plants of the cultivar Leonardo have red purple-colored flowers. In addition, plants of the new Kalanchoe flower about two weeks later than plants of the cultivar Leonardo.

Plants of the new Kalanchoe differ from plants of the male parent, the cultivar Alexandra, in the following characteristics:

1. Plants of the new Kalanchoe are more compact than plants of the cultivar Alexandra.
2. Plants of the new Kalanchoe have multi-petalled flowers whereas plants of the cultivar Alexandra have about four petals per flower.
3. Flowers of plants of the new Kalanchoe are pink in color whereas flowers of plants of the cultivar Alexandra are yellow in color.

Plants of the new Kalanchoe differ from plants of the cultivar Middler, disclosed in a U.S. Plant Patent application filed concurrently, primarily in flower color.

BRIEF DESCRIPTION OF THE PHOTOGRAPH

The accompanying colored photograph illustrates the overall appearance of the new Kalanchoe, showing the colors as true as it is reasonably possible to obtain in colored reproductions of this type. Colors in the photograph may differ slightly from the color values cited in the detailed botanical description which accurately describe the colors of the new Kalanchoe. The photograph comprises a side perspective view of a typical plant of 'La Douce' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and for the description were grown during the spring in De Lier, The Netherlands, in a glass-covered greenhouse.

During the production of the plants, day temperatures ranged from 19 to 26° C.; night temperatures ranged from 20 to 21° C.; and light levels ranged from 10,000 to 50,000 lux. Unrooted cuttings were directly stuck in 10-cm containers and received long day/short night conditions (more than 14 hours of light) for about three weeks; plants then received photoinductive short day/long night conditions (minimum 14 hours darkness) until flowering. Plants were about 14 weeks old from an unrooted cutting when the photograph and the description were taken.

Botanical classification: *Kalanchoe blossfeldiana* cultivar La Douce.

Parentage:

*Female, or seed, parent.*—*Kalanchoe blossfeldiana* cultivar Leonardo, disclosed in U.S. Plant Pat. No. 13,365.

*Male, or pollen, parent.*—*Kalanchoe blossfeldiana* cultivar Alexandra, disclosed in U.S. Plant Pat. No. 10,262.

Propagation:

*Type cutting.*—Terminal vegetative cuttings.

*Time to initiate roots.*—Summer: About 10 days at 21° C. Winter: About 14 days at 21° C.

*Time to produce a rooted cutting.*—Summer: About 21 days at 21° C. Winter: About 28 days at 21° C.

*Root description.*—Numerous; fine; fibrous; greyed white in color.

*Rooting habit.*—Freely branching.

Plant description:

*Form.*—Upright and uniform plant habit. Very freely flowering with numerous compound cymes. Inverted triangle with rounded crown. Appropriate for 10 to 15-cm containers.

*Crop time.*—About 13 to 16 weeks: three to four weeks under long day/short night conditions followed by ten to twelve weeks of short day/long night conditions. Moderate growth rate.

*Plant height at flowering.*—About 17 cm.

*Plant diameter at flowering.*—About 16 cm.

*Branching habit.*—Freely branching; typically seven to eight lateral branches develop per plant. Pinching (removal of terminal apex) is not required but will enhance lateral branch development.

*Lateral branch description.*—Length: About 11 to 15 cm. Diameter: About 2 to 5 cm. Internode length: About 2 to 3 cm. Aspect: Erect. Strength: Moderately strong. Texture: Smooth, glabrous. Color: 147A.

*Foliage description.*—Leaves simple, opposite, generally symmetrical. Quantity per plant: About 8 to 13 mature leaves and 14 to 22 generative leaves. Length: About 10 cm. Width: About 7.5 cm. Shape: Ovate. Apex: Obtuse. Base: Acute. Margin: Slightly crenate. Texture, upper and lower surfaces: Leathery, glabrous and succulent. Color: Developing and fully expanded leaves, upper surface: 147A; glossy. Developing and fully expanded leaves, lower surface: 147B. Venation, upper surface: 147A to 147B. Venation, lower surface: 147B. Petiole length: About 1.5 cm. Petiole diameter: About 4 mm by 8 mm. Petiole color: Upper surface: 147A to 147B. Lower surface: 147B.

Flower description:

*Flower type and habit.*—Multi-petalled flowers arranged in compound dichasial cymes that arise from leaf axils. Freely flowering; more than 25 open flowers per lateral branch and more than 150 open flowers per plant. Flowering continuously for at least seven weeks. Flowers persistent. Flowers not fragrant.

*Natural flowering season.*—Plants of the new Kalanchoe initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about ten to twelve weeks are required. Actual time to flower is primarily dependent upon temperature and light intensity.

*Post-production longevity.*—Excellent post-production longevity; plants maintain good foliage and flower substance for about 53 days under interior environmental conditions. Individual flowers last about 22 days on the plant.

*Flower diameter.*—About 1.9 cm.

*Flower height.*—About 1.3 cm.

*Flower buds.*—Shape: Initially oblong, becoming tubular ovoid with development. Length: About 1.3 cm. Width: About 6 mm. Color: Initially 138C becoming closer to 63D just before opening.

*Petals.*—Quantity: About 21 to 28 per flower arranged in three to five rows. Length: About 8 mm. Width: About 6 mm. Aspect: Flat to slightly upright. Shape: Ovate. Apex: Acute. Margin: Entire. Texture, upper and lower surfaces: Glabrous, smooth. Color: When opening, upper surface: 62A. When opening, lower surface: 69C. Fully opened, upper surface: 62A. Fully opened, lower surface: 69B.

*Sepals.*—Quantity: Four fused at base. Length: About 5 mm. Width: About 2 mm. Aspect: Erect. Shape: Oblong. Apex: Acute. Base: Rounded. Margin: Entire. Texture, upper and lower surfaces: Glabrous, smooth. Color, upper and lower surfaces: 138D.

*Peduncles.*—Length: About 6 mm. Diameter: About 1 mm. Aspect: Erect. Strength: Strong, rigid. Texture: Smooth, glabrous. Color: 138B.

*Reproductive organs.*—Stamens: Quantity per flower: Eight. Anther shape: Elliptic; flat. Anther size: About 0.3 mm. Anther color: Close to 150D. Pollen amount: Scarce. Pollen color: Close to 12 A. Pistils: Quantity per flower: Four. Style length: About 1 mm. Style color: 138D. Stigma shape: Flat, rounded. Stigma color: 8D. Ovary color: 138D. Seed: Length: About 0.1 mm. Diameter: About 0.05 mm. Color: Close to 166C.

Disease/pest resistance: Plants of the new Kalanchoe have not been observed to be resistant to pathogens and pests common to Kalanchoes.

Temperature tolerance: Plants of the new Kalanchoe have been observed to tolerate low temperatures of 12° C. and high temperatures of 35° C.

Garden performance: Plants of the new Kalanchoe have been observed to perform well in the garden and are tolerant to rain and wind.

It is claimed:

1. A new and distinct cultivar of Kalanchoe plant named 'La Douce', as illustrated and described.

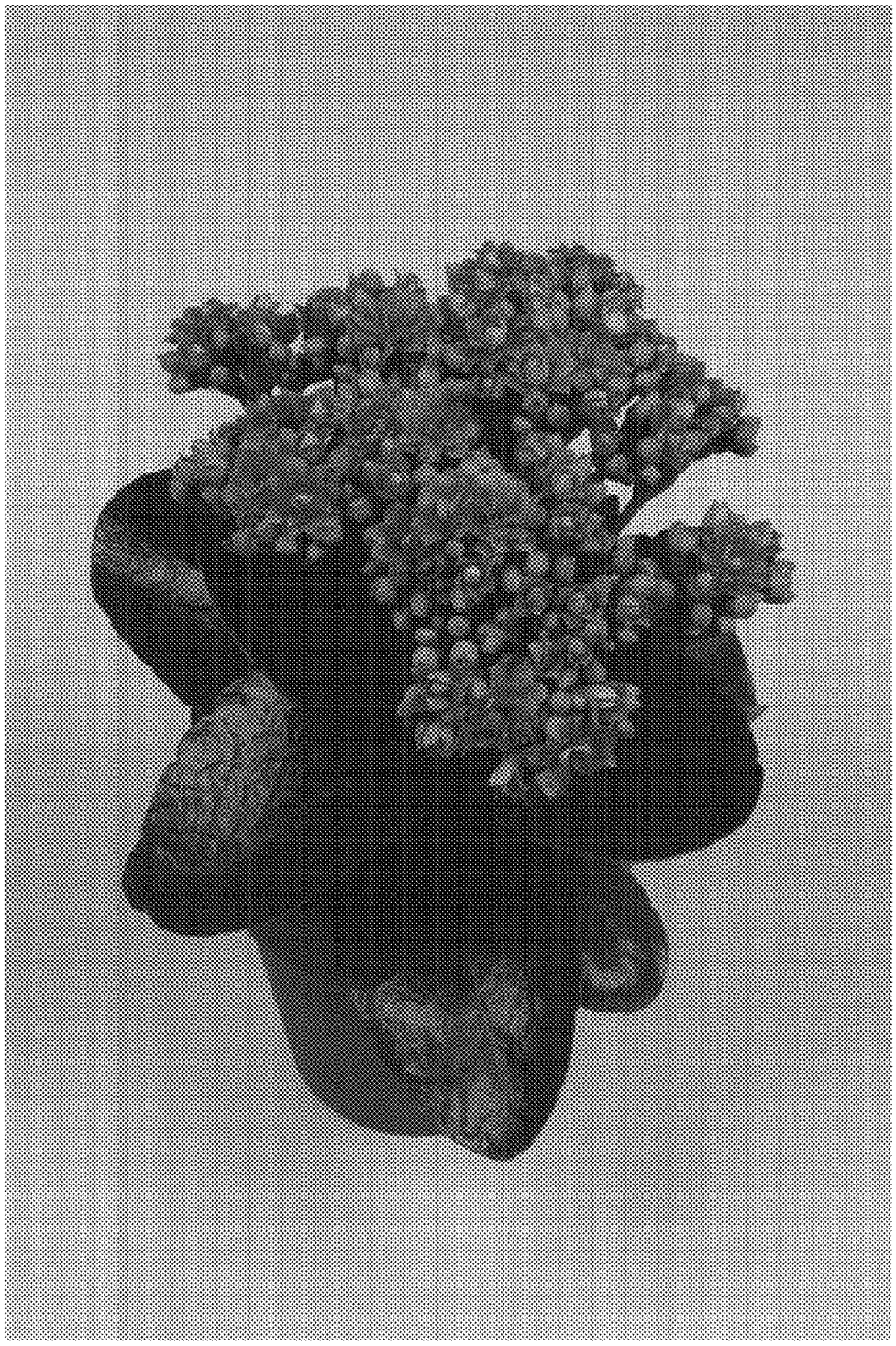

* * * * *